(12) United States Patent
Latham

(10) Patent No.: US 7,588,673 B2
(45) Date of Patent: Sep. 15, 2009

(54) ELECTROPHORESIS CASSETTE WITH SEALING AND CLOSURE FEATURES

(75) Inventor: Matthew Latham, Dixon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 688 days.

(21) Appl. No.: 11/227,321

(22) Filed: Sep. 14, 2005

(65) Prior Publication Data

US 2007/0056854 A1   Mar. 15, 2007

(51) Int. Cl.
*G01N 27/453* (2006.01)
(52) U.S. Cl. .................................. 204/616; 204/618
(58) Field of Classification Search ......... 204/616–620, 204/466, 467
See application file for complete search history.

(56) References Cited

U.S. PATENT DOCUMENTS

| | | | | |
|---|---|---|---|---|
| 4,957,613 A | * | 9/1990 | Schuette | 204/618 |
| 5,186,807 A | * | 2/1993 | Sanford et al. | 204/618 |
| 5,192,408 A | | 3/1993 | Scott | |
| 5,569,369 A | * | 10/1996 | Leffler et al. | 204/620 |
| 5,707,506 A | * | 1/1998 | Douthart et al. | 204/622 |
| 5,938,906 A | * | 8/1999 | Moi et al. | 204/465 |
| 6,110,340 A | * | 8/2000 | Lau et al. | 204/467 |
| 6,162,342 A | | 12/2000 | Perez et al. | |
| D443,068 S | * | 5/2001 | Manusu et al. | D24/233 |
| 6,231,741 B1 | * | 5/2001 | Tuurenhout et al. | 204/618 |
| 6,398,933 B1 | * | 6/2002 | Scott | 204/466 |
| 6,451,193 B1 | | 9/2002 | Fernwood et al. | |
| 2003/0125466 A1 | * | 7/2003 | Chmielewski | 525/199 |
| 2004/0020515 A1 | | 2/2004 | Tolosko et al. | |
| 2005/0176135 A1 | | 8/2005 | Jones | |

* cited by examiner

*Primary Examiner*—Alex Noguerola
(74) *Attorney, Agent, or Firm*—Townsend and Townsend and Crew LLP.; M. Henry Heines

(57) ABSTRACT

Slab gel electrophoresis cassettes constructed from two flat rectangular plates, with features that allow the plates to be joined parallel to and facing each other with a gap between them that is sealed at the sides and open at the top and bottom for access to upper and lower electrodes, respectively, are improved by two independent features. The first is the integration of an elastomeric gasket to the surface of one of the two plates to ensure a liquid-tight seal, while the second is the inclusion of edge engaging members that are mounted to one plate and engage an opposing edge of the other plate. The engaging members are manually engaged and released at will. In preferred constructions, the gasket is a strip that extends along the two sides and bottom of one of the plates, and each engaging member is pivotally and resiliently mounted to achieve a snap-type engagement.

12 Claims, 3 Drawing Sheets

US 7,588,673 B2

ELECTROPHORESIS CASSETTE WITH SEALING AND CLOSURE FEATURES

BACKGROUND OF THE INVENTION

1. Field of the Invention

This invention resides in the field of slab gel electrophoresis and particularly in the design and construction of cassettes for holding a slab gel during electrophoresis.

2. Description of the Prior Art

Electrophoresis is widely used in both the clinical laboratory and the research laboratory as a rapid and effective separation process for analyzing complex, biologically derived mixtures. One of the media in which electrophoresis is commonly performed is a slab gel, which permits the simultaneous analysis of several samples by dividing the slab into lanes and using one lane for each sample. The use of a slab gel in this manner affords not only speed and an efficient use of time, but also eliminates many of the problems that commonly arise when separate procedures are performed on each of a series of samples, such as nonuniformity due to variations in gel quality and operating conditions, and the risk of operator error. The electropherograms produced in slab gels can be read and interpreted visually, allowing the user to readily identify the components present in the sample by observing the locations of the bands.

Slab gels are typically retained in cassettes that can be readily inserted in, and removed from, an electrophoresis cell which contains the components needed for imposing an electric current across the gel. A cassette is typically constructed from two plastic plates joined together with appropriate spacers to form a gap of specified width between the plates for the gel, with sealing features to prevent leakage of the gel-forming monomer mixture during gel casting as well as the gel itself during electrophoresis. In many cases, gels are pre-cast in cassettes by manufacturers to a variety of specifications. In others, users cast their own gels in cassettes immediately prior to use. Whether the gel is pre-cast or not, the removal of the gel from the cassette for staining, recordation, quantification, or other procedures following the separation requires the cassette to be opened to provide access to the gel. The opening of the cassette can be a delicate operation since it involves breaking the seals around the gel and separating the plates without damaging or distorting the gel. The seals must therefore be capable of being opened or broken and yet provide a liquid-tight seal along the edges of the two plates to assure product uniformity and reliability. Ultrasonic welding is often used as a means of joining the plates together since the weld is readily broken when the gel is ready for removal. Ultrasonic welding is a delicate process however and requires a careful balance between achieving an effective seal and allowing the user to break the seal when the separation is completed without damaging the plates themselves which often results in damage to the gel.

SUMMARY OF THE INVENTION

The present invention resides in slab gel electrophoresis cassettes that have an added measure of sealing security. Like conventional slab gel cassettes, the cassettes of this invention are constructed from two flat rectangular plates that are joined together parallel to and facing each other with a gap between the plates for the gel, while closing the gap at the side edges of the plates and leaving the gap open at the top and bottom edges for access to upper and lower electrodes through respective buffer solutions. The added sealing of the present invention is supplied by a gasket of elastomeric material that is affixed to one of the two plates to form an edge seal between the plates when the plates are joined together. The elastomeric gasket is used in conjunction with any method of joinder of the plates, examples of which are welding, chemical bonding, the use of disposable materials such as adhesive tape, or the use of manually operable closures such as clips or otherwise engageable parts. Depending on the construction of the plates and the cassette as a whole, the gasket extends along at least the two side edges of one plate, and in some cases along the bottom edge as well.

The invention further resides in slab gel cassettes that are securely joined yet readily opened by hand to expose and remove the gel inside, and then re-closed and re-sealed if desired for casting a fresh gel and performing new separations. The cassettes in this aspect of the invention are likewise constructed from two flat rectangular plates, with features that allow the plates to be joined parallel to and facing each other with a gap between them, sealed at the side edges and open at the top and bottom. The manually releasable joining features introduced by this invention are edge engaging members that are mounted to one plate and engage an opposing edge of the other plate in a manner that allows the user to engage the plates with these members and release them manually at will. In preferred embodiments, each edge engaging member has an inverted shoulder, i.e., a shoulder facing the plate to which the member is mounted, that hooks or grasps the edge of the opposing plate. IN these embodiments, the engaging member is pivotally mounted to allow the inverted shoulder to be pivoted manually into and out of engagement with the opposing edge. Other preferred features are a sloping surface on each engaging member leading to the inverted shoulder and a resilient mounting of the engaging member. These last-mentioned features allow the user to snap the member into engagement, i.e., to snap the plates together by simply pressing the plates against each other with their edges aligned.

These and other features of the invention in its various embodiments will be apparent from the description that follows.

DETAILED DESCRIPTION OF THE INVENTION AND PREFERRED EMBODIMENTS

Figure 1:
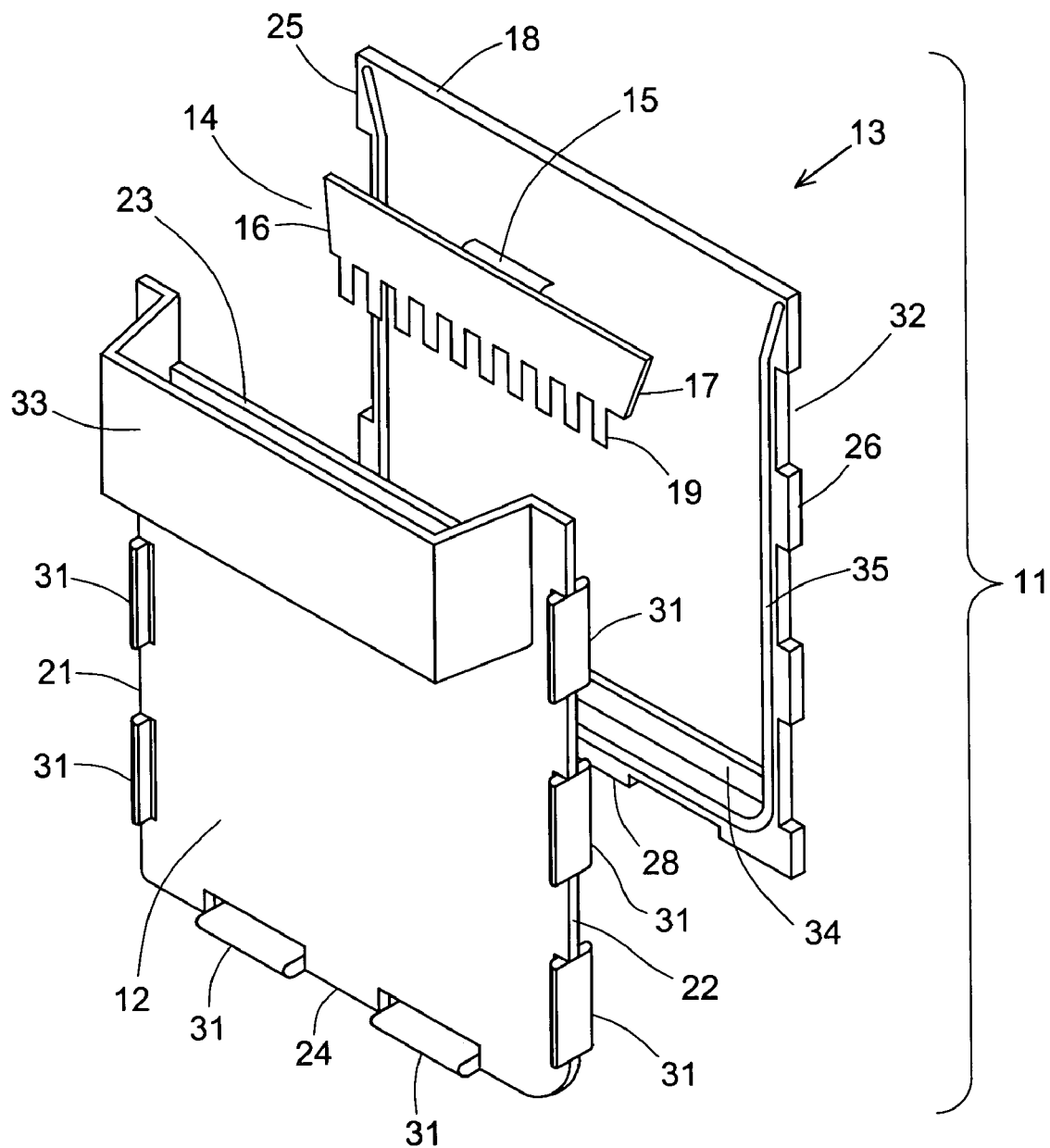
FIG. 1 is an exploded view in perspective of one example of a cassette in accordance with the present invention.

The elastomeric gasket of this invention can be formed of any resiliently deformable elastomer that is inert to the gel and the gel-forming monomers that the gasket will contact in the cassette, and particularly that does not inhibit the polymerization of the monomers to form the gel. Examples of elastomeric materials that can used as the gasket are natural rubber, styrene-butadiene rubber, isoprene rubber, EPDM rubber, butyl rubber, nitrile rubber, chloroprene rubber, silicones, fluoropolymers, polysulfide rubber, and polyurethanes. Trade names associated with some of these products are SANTOPRENE® (a polyolefin-based thermoplastic vulcanizate, available from Advanced Elastomer Systems, LP, Akron, Ohio, USA), VERSALON® (a rayon-polyester blend, available from Tyco Healthcare Group LP, Mansfield, Mass., USA), and elastomers from DuPont Dow Elastomers, Wilmington, Del., USA, including VITON® (fluoroelastomer), KALREZ® (perfluoroelastomer), HYPALON® (chlorosulfonated polyethylene), and ACSIUM® (chlorosulfonated polyethylene). Other examples will be readily apparent to those with current familiarity with the elastomer industry.

The gasket can consist of discrete strips along separate edges of the cassette or a continuous strip along the side edges and the bottom edge. The gasket is secured to one of the two plates by any of various means of attachment, examples of which are chemical bonding and the use of adhesives or two-sided tape. The gasket is preferably integrated with, i.e., permanently secured to, the plate, again by chemical bonding or the use of adhesives. It is further preferred that the gasket does not by itself establish the gap width between the plates; the gap width is preferably established by a spacer of precise and non-deformable thickness, for example either a strip of inert material to be inserted between the plates or a ridge of a fixed height on one or both of the plates. The gasket when not compressed will have a thickness greater than the spacer, so that when the opposing plate abuts the spacer to set the gap width, the gasket will be flattened to a limited degree.

As noted above, the integrated elastomeric gasket can be used in conjunction with any method of joining the two plates of the cassette together. The joining means can thus be closures that once opened cannot be reclosed to rejoin the plates for re-use, such as for example ultrasonic welds, and closures that can be reclosed after opening, such as clips or other mechanical engaging members. In either case, the elastomeric gasket forms a liquid-tight seal along the periphery of the gel in a manner that leaves the areas exposed that are needed by the user for sample loading and during the electrophoresis for access of the electrode buffers to the gel.

In aspects of the invention involving the use of edge engaging members, two or more such members will typically be used. The number and distribution of the members are not critical to the invention, however, or to the operation of the cassette. Any number and arrangement that will provide a stable and secure attachment of the plates to each other will suffice. Preferably, edge engaging members are present on the two side edges of the plates, and most preferably at the bottom edge as well. In these cassettes, the "side edges" are defined as those edges that are parallel to the direction of the electric potential through the gel and hence to the direction of migration of the solutes during electrophoresis, and the "end edges" or "top edge" and "bottom edge" are the exposed edges at the two ends of the solute migration path, transverse to the direction of the electric potential. The "top edge" is the edge at which the samples are loaded, and the "bottom edge" is the edge toward which the solutes migrate during electrophoresis. Exposure of the gel at the bottom edge can be achieved by the avoiding or removing any barrier along the bottom border of the gap or by forming a slit in one of the plates that extends the full width of the plate and exposes a narrow lateral strip of the gel surface. In all cases, the top edge is preferably left fully accessible to allow the user to load samples into the gel at any location along the width of the gel.

Cassettes of this invention preferably contain at least one edge engaging member on each of the two side edges of the cassette, and at least one on the bottom edge. The edge engaging members are either all mounted to one of the plates or are divided among the two plates. For manufacturing and handling convenience, the members can all be mounted to one plate. When these edge engaging members are present, they can serve as the only means of securing the two plates together, the two plates being completely separable by disengaging the members. In alternative constructions, still within the scope of this invention, the two plates can be joined along one edge, preferably a side edge, in a hinge-type connection permitting the plates to be opened at the opposing edge for exposure of the inner surfaces of the plates and removal of the gel. The edge engaging members are then mounted at the side opposite the hinged side, and preferably also along the bottom edge.

While the invention is susceptible to a wide range of configurations, geometries, and features, either in connection with the edge engaging members or other features of the cassette, an understanding of the invention in its full scope is most readily achieved by a detailed study of one embodiment. Such an embodiment is shown in the drawings and described below.

In the perspective view of FIG. 1, the cassette 11 is shown as a pair of plates, which are referred to for convenience as a front plate 12 and a back plate 13, and are shown separated so that their features are visible. An accessory part, commonly known as a sample comb 14 due to its shape, is included in the assembly for forming sample wells in the gel. The comb 14 has a tab 15 that can be grasped by the user for purposes of inserting the comb between the plates as the gel is being formed and for removing it to allow access to the wells once the gel is formed. The tab can also serve as a site of engagement in automated operations involving the cassette. The comb contains angled end edges 16, 17 that mate with angled ridges (not shown) on the inner surface of the front plate 12 to center the comb with its teeth 19 extending into the gap.

The front plate 12 has two side edges 21, 22 and two end edges including a top edge 23 and a bottom edge 24. The back plate 13 likewise has two side edges 25, 26, a top edge 18, and a bottom edge 28. Mounted to the front plate are eight edge engaging members 31, three along each of the two side edges 21, 22 (of those along the left side edge 21, only two are visible), and two along the bottom edge 24. The back plate 13 has indentations 32 in its side and bottom edges at locations opposite the locations of the edge engaging members 31 on the front plate 12. The edge engaging members 31 engage the indented edges.

The front and back plates 12, 13 are both shaped to expose the top and bottom edges of the gel that will reside between them. The two plates are of unequal height, with the front plate 12 the shorter of the two. The top edge 23 of the front plate 12 thus resides below the top edge 18 of the back plate 13 when the two are secured to each other by the edge engaging members 31. The front plate 12 has a protrusion 33 extending outward from its outer surface, bordered on three sides by walls as high as the top edge 18 of the back plate and on the fourth side by the wall with the relatively low top edge 23. Thus, when the plates are joined, the protrusion 33 combines with the upper end of the back plate 13 to form a reservoir which serves as a chamber for an upper electrode buffer solution. With the gel extending only up as far as the top edge 23 of the front plate, the upper edge of the gel resides within the reservoir and is immersed in the upper electrode buffer solution when the chamber is filled with the solution. At the bottom end of the cassette, a slot 34 is present in the back plate 13, exposing a strip of the gel along the lower edge of the gel. The elastomeric gasket described above appears in this embodiment as a strip 35 of gasket material in a U-shaped configuration along the two sides and bottom of the back plate 13. The strip 35 passes below the slit 34 to avoid interfering with the exposure of the lower end of the gel.

Figure 2:
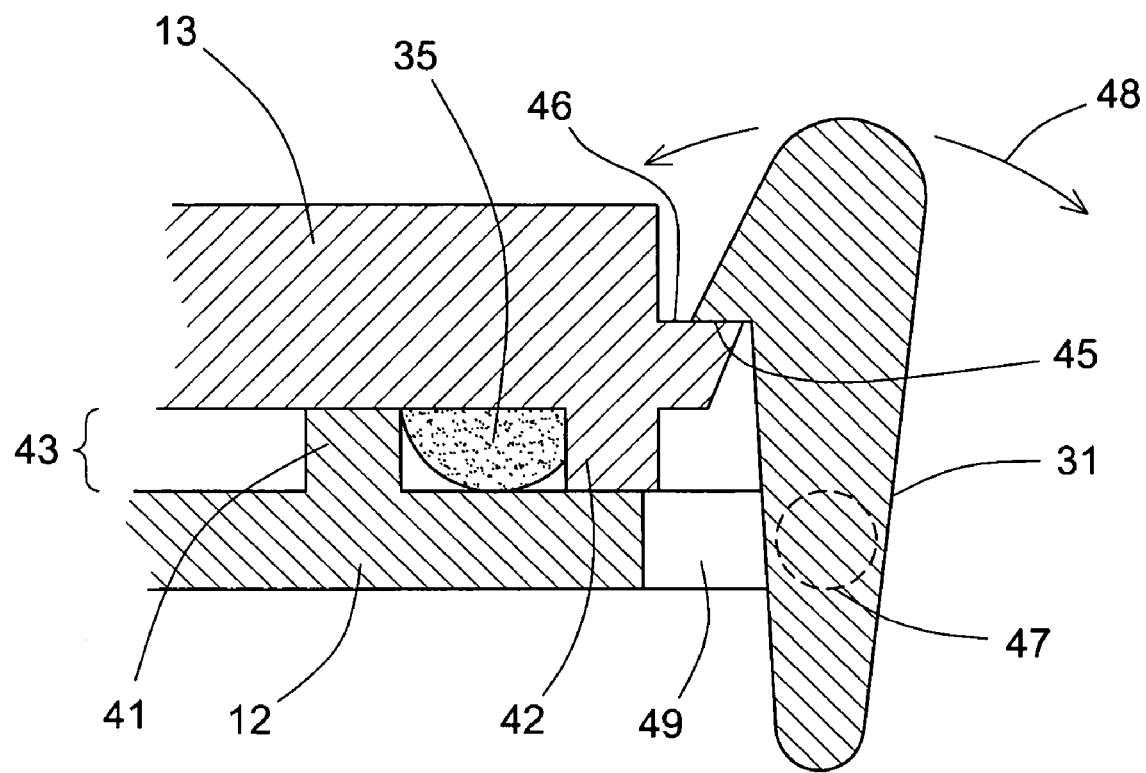
FIG. 2 is a cross section of a portion of one edge of the cassette of FIG. 1 at the location of an edge engaging member.

The cross section of FIG. 2 is taken at the location of any one of the edge engaging members. In this view, the front plate 12 and back plate 13 are joined and secured together by the edge engaging member 31. Raised ridges 41, 42 on inner surfaces of the front and back plates, respectively, establish the width of the gap 43 between the plates, and the gasket strip 35 resides between the two ridges 41, 42 and is affixed to or integrated with the back plate 13. The edge engaging member 31 is mounted to the front plate 12 and has an inverted shoulder 45 that faces back toward the front plate. The back plate 13 likewise has a shoulder 46 that is engaged by the inverted shoulder 45 of the engaging member, the inverted shoulder 45 hooking over the back plate at this shoulder 46. A short connecting web 47, shown in dashed lines, joins the engaging member 31 to the front plate, the web being deformable to allow the engaging member 31 to pivot over a small arc indicated by the arrow 48. An opening 49 in the front plate provides clearance for the engaging member as it pivots.

Figure 3:
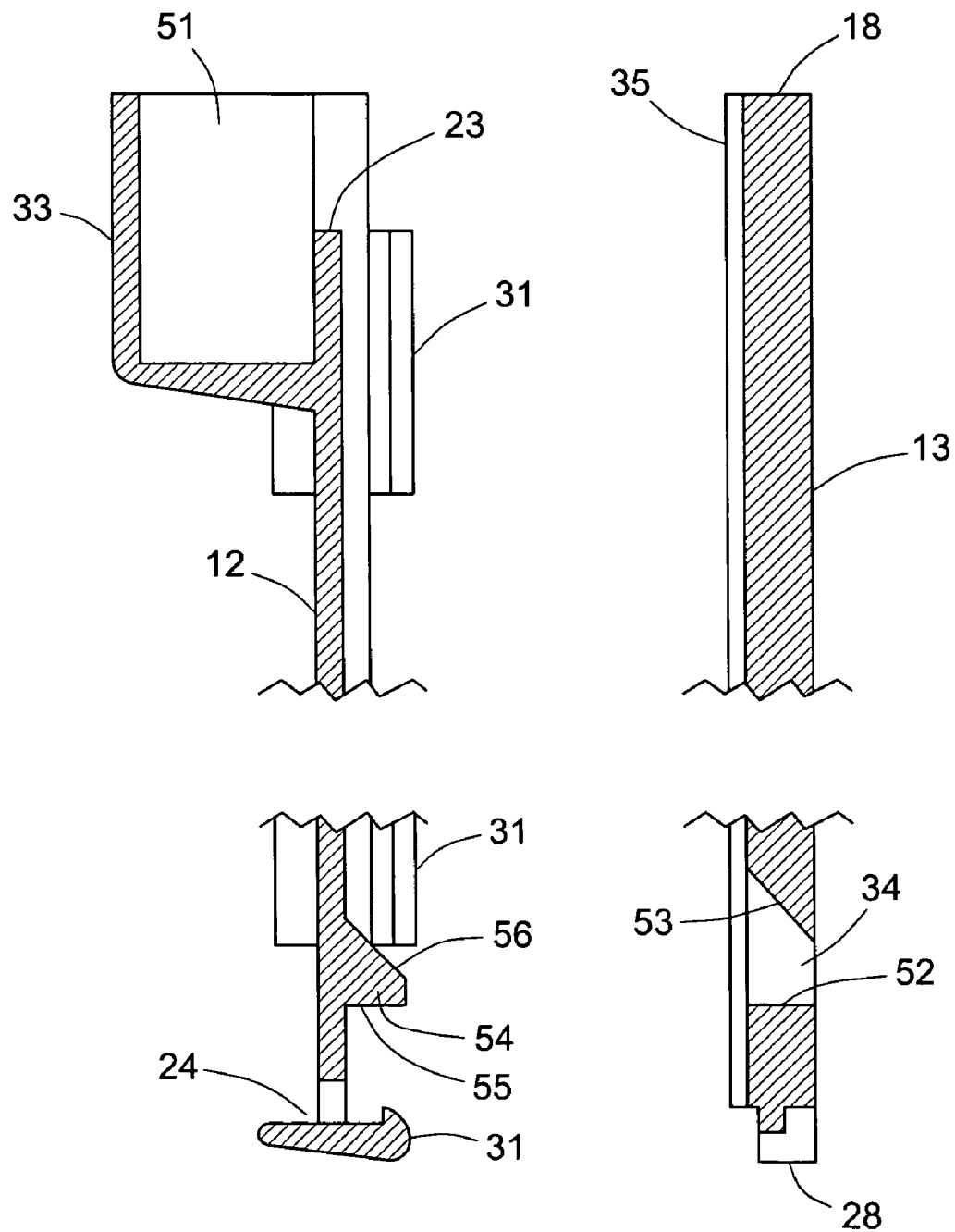
FIG. 3 is a cross section of the separated front and back plates of the cassette of FIG. 1.

FIG. 3 is a cross section of the front plate 12 and back plate 13 showing the features of these plates that provide for electrode access to the gel. The two plates are separated in this view for clarity. The protrusion 33 extending from the outer side of the front plate 12 forms the upper electrode buffer chamber 51 when the front and back plates are joined. The gel terminates at the top edge 23 of the front plate 12 while the walls of the upper electrode buffer chamber 51 when the two plates are joined extend to the top of the protrusion 33 and the top edge 18 of the back plate 13 and are sealed at the sides by the gasket 44. Near the bottom of the back plate 13 is the slit 34 extending the width of the plate, the lower edge 52 of which is transverse (perpendicular) to the planes of the plate surfaces while the upper edge 53 is angled. The front plate 12 has a ridge 54 on its inner surface protruding toward the back plate and likewise extending the full width of the plate. The lower edge 55 of the ridge is perpendicular to the planes of the plate surfaces and at a location where it contacts the lower edge 52 of the slit 34 in the back plate, while the upper edge 56 of the ridge is angled at the same angle as the upper edge 53 of the slit 34. The upper edge 56 of the ridge is lower than the upper edge 53 of the slit, so that these two angled edges do not contact each other when the plates are joined, but instead leave an open angled passage between them. During electrophoresis, the lower ends 24, 28 of the combined plates are immersed in a reservoir (not shown) containing a lower electrode and a lower electrode buffer solution, while an upper electrode (not shown) is placed in the upper electrode buffer chamber 51 together with an upper electrode buffer solution.

The foregoing is offered for purposes of illustration. Further variations, configurations, and additional components that fall within the scope of the invention will be readily apparent to those skilled in the art.

What is claimed is:

1. In a slab gel electrophoresis cassette comprising:
    first and second plates, both substantially rectangular with side edges and end edges, and
    means for joining said plates parallel to and facing each other with a gap of preselected width between said plates while closing said gap along said side edges and leaving said gap open at said end edges for electrode buffer access, the improvement in which said means for joining said plates comprise a plurality of edge engaging members distributed along said side edges, each said edge engaging member mounted to one plate to engage an opposing side edge of the other plate in a manually releasable manner, wherein each of said edge engaging members has an inverted shoulder to receive said opposing side edge and is pivotally mounted to pivot said inverted shoulder into and out of engagement with said opposing side edge.

2. The slab gel electrophoresis cassette of claim 1 wherein said means for joining said plates further comprises at least one edge engaging member along one of said end edges.

3. The slab gel electrophoresis cassette of claim 2 wherein each of said edge engaging members has an inverted shoulder to receive said opposing side or end edge and is pivotally mounted to pivot said inverted shoulder into and out of engagement with said opposing side or end edge.

4. The slab gel electrophoresis cassette of claim 2 wherein said edge engaging members are all mounted to said first plate.

5. The slab gel electrophoresis cassette of claim 1 wherein each of said edge engaging members has an inverted shoulder to receive said opposing side edge and said opposing side edge has a shoulder to receive said inverted shoulder.

6. The slab gel electrophoresis cassette of claim 1 wherein each of said edge engaging members has an inward-facing sloping surface which, when contacted with said opposing side edge when said plates are pressed together, causes said edge engaging member to open and receive said opposing side edge.

7. The slab gel electrophoresis cassette of claim 1 wherein said edge engaging members are resiliently mounted.

8. The slab gel electrophoresis cassette of claim 1 wherein said edge engaging members are all mounted to said first plate.

9. The slab gel electrophoresis cassette of claim 1 wherein said means for joining said plates parallel to and facing each other with a gap of preselected width while closing said gap along said side edges and leaving said gap open at said end edges comprise a gasket of resiliently deformable material affixed to one of said plates.

10. The slab gel electrophoresis cassette of claim 9 wherein said resiliently deformable material is an elastomer.

11. The slab gel electrophoresis cassette of claim 10 wherein said elastomer is a member selected from the group consisting of fluoropolymers and polyolefin-based thermoplastic vulcanizates.

12. The slab gel electrophoresis cassette of claim 10 wherein said gasket is bonded to one face of one of said plates.

* * * * *